United States Patent
Evans et al.

(10) Patent No.: US 9,133,326 B2
(45) Date of Patent: Sep. 15, 2015

(54) MINERALISED COMPOSITE MATERIAL COMPRISING CHITIN AND CALCIUM CARBONATE

(71) Applicant: Victoria Link Limited, Wellington (NZ)

(72) Inventors: Natasha Helen Evans, Wellington (NZ); Kathryn Mavis McGrath, Wellington (NZ)

(73) Assignee: Victoria Link Limited, Wellington (NZ)

( * ) Notice: Subject to any disclaimer, the term of this patent is extended or adjusted under 35 U.S.C. 154(b) by 0 days.

(21) Appl. No.: 14/365,066

(22) PCT Filed: Dec. 12, 2012

(86) PCT No.: PCT/IB2012/057197
§ 371 (c)(1),
(2) Date: Jun. 12, 2014

(87) PCT Pub. No.: WO2013/088347
PCT Pub. Date: Jun. 20, 2013

(65) Prior Publication Data
US 2014/0371354 A1  Dec. 18, 2014

Related U.S. Application Data

(60) Provisional application No. 61/570,010, filed on Dec. 13, 2011.

(51) Int. Cl.
*C08L 5/08* (2006.01)
*A61L 27/44* (2006.01)

(52) U.S. Cl.
CPC .............. *C08L 5/08* (2013.01); *A61L 27/446* (2013.01); *A61L 2420/04* (2013.01); *A61L 2430/02* (2013.01); *A61L 2430/12* (2013.01); *C08L 2314/00* (2013.01)

(58) Field of Classification Search
None
See application file for complete search history.

(56) References Cited

U.S. PATENT DOCUMENTS

2004/0131562 A1   7/2004   Gower et al.

OTHER PUBLICATIONS

Addadi et al., "Interactions between acidic proteins and crystals: Stereochemical requirements in biomineralization," *Proc. Natl. Acad. Sci. USA* 82:4110-4114, Jun. 1985.
Brugnerotto et al., "An infrared investigation in relation with chitin and chitosan characterization," *Polymer* 42: 3569-3580, 2001.
Hosoda et al., "Thin-Film Formation of Calcium Carbonate Crystals: Effects of Functional Groups of Matrix Polymers," *Chem. Mater.* 13:688-693, 2001.
Kato et al., "Layered Thin-Film Composite Consisting of Polymers and Calcium Carbonate: A Novel Organic/Inorganic Material with an Organized Structure," *Chemistry Letters* 29:186-187, 2000.
Kitano, "The Behavior of Various Inorganic Ions in the Separation of Calcium Carbonate from a Bicarbonate Solution," *Bull. Chem. Soc. Jpn.* 35(12):1973-1980, 1962.

(Continued)

*Primary Examiner* — Vu A Nguyen
(74) *Attorney, Agent, or Firm* — Seed IP Law Group PLLC (57) ABSTRACT

The invention relates to a mineralized composite material and methods of forming such a material. The process comprises mineralization of a chitin template with calcium carbonate. The mineralized composite material of the invention has similar properties to the natural material nacre.

20 Claims, 4 Drawing Sheets

(56) References Cited

OTHER PUBLICATIONS

Munro et al., "Biomimetic mineralisation of polymeric scaffolds using a combined soaking and Kitano approach," *Dalton Trans.* 40:9259-9268, 2011.

Taguchi et al., "Hydroxyapatite Formation on/in Poly(vinyl alcohol) Hydrogel Matrices Using a Novel Alternate Soaking Process," *Chemistry Letters* 8:711-712, 1998.

Tang et al., "Nanostructured artificial nacre," *Nature Materials* 2:413-418, Jun. 2003.

Tawashi et al., In vitro Formation of Calcite Concretions, *Experientia* 30(10:1153-1154, 1974.

Wu et al., "Crystallization of Calcium Carbonate on Chitosan Substrates in the Presence of Regenerated Silk Fibroin," *Langmuir* 27:2804-2810, 2011.

Zhang et al., "Synthesis of Calcium Carbonate-Chitosan Composites via Biomimetic Processing," *Journal of Applied Polymer Science* 56:687-695, 1995.

MINERALISED COMPOSITE MATERIAL COMPRISING CHITIN AND CALCIUM CARBONATE

FIELD OF THE INVENTION

The invention relates generally to a mineralised composite material, and methods of forming it.

BACKGROUND

One of the most keenly investigated structural biomaterials that promises great potential in a variety of technological and scientific areas is nacre. Nacre, also known as mother of pearl, is an organic-inorganic composite material produced by certain molluscs such as bivalves, gastropods and cephalopods. The nacre is continually deposited on the inner surface of the shell, protecting the soft tissues from damage by parasites and dirt by entombing these in layers of nacre.

Nacre has long fascinated scientists for its remarkable mechanical properties of strength and toughness attained from inferior performing starting materials. Nacre is made of platelets of aragonite (a polymorph of $CaCO_3$) arranged in, on average, parallel layers. These layers are separated by an organic matrix composed of elastic biopolymers such as chitin, lustrin and silk-like proteins.

The remarkable properties of nacre are a consequence of its detailed nanoscale assembly and construction, as well as ionic crosslinking of the tightly folded biopolymers in the matrix (Tang Z, Kotov N, Maganov S, Ozturk B., "Nanostructured artificial nacre", *Nature Materials*, 2003, 2, 413-418).

Nacre is a near ideal platelet composite that is strong in the x (on the platelet face) and y planes (90 degree angle from the face) and is plastic at increasing strain (beyond 0.01). The highly ordered arrangement of crystalline platelets 200-900 nm thick gives the macrostructure its strength. Intercalated matrix proteins, 10-50 nm thick, provide the nacre with elasticity and fracture-stopping capabilities. Fractures are deflected through the matrix which transfers the applied loads at the fracture point.

Generally, synthetic composites cannot be fabricated with the same sophisticated microstructures that enable natural biomaterials such as nacre to perform. Biomineralisation usually occurs via a slow precipitation at close to ambient temperatures and pressures. This process is highly influenced by specialised biomolecules, usually proteins that may absorb on specific crystallographic faces to decrease the growth rate of these faces, giving the crystal a specific morphology. In biomineralisation, the organism can use special compartments of crystallisation to control the temperature, pH and ion concentration of the crystallisation environment.

Many researchers are developing ways of producing nacre-like materials using the substrates and molecular processes involved in nacre shell formation. Nacre formation has been mimicked by exposing specified quantities of key acidic macromolecules and accessory mineral ions such as magnesium ions to chitosan templates to modulate calcium carbonate crystal morphology, size and polymorph.

Replicating the slow process of biomineralisation in vitro is difficult, but several methods of mineralising matrices have been developed, to generate nacre-like composite materials.

In the ammonium carbonate diffusion method, ammonium carbonate vapour is diffused over organic surfaces leading to rapid calcium carbonate precipitation (Tawashi R, Bisaillon S, Wolter K. In vitro formation of calcite concretions. *Experientia*, 1974, 30(10) 1153-1154; Addadi L, Weiner S. Interaction between acidic proteins and crystals: Stereochemical requirements in biomineralization. *Proceedings of the National Academy of Science USA*, 1985, 82, 4110-4114).

Another method is double diffusion, where solutions containing the respective cation and anion of the target mineral are separated by a polymer or hydrogel template. The diffusion through the template induces mineralisation within the template. However, the formation of crystals within the template can lead to limited growth at the periphery due to decreased diffusion of the ions through the material.

In US patent application US 2007/0225328, Fritz et al. describe using double diffusion of calcium and carbonate ions to mineralise a template comprising the water-insoluble matrix of mussel, snail or other chitin-containing protecting armament of a sea water animal. The double diffusion method involves counter-diffusion of two solutions across an insoluble matrix at opposite sides. A decrease in pH affects the surface properties of the matrix, encouraging calcium carbonate nucleation and growth. The template is prepared for mineralisation by cleaning and crushing the chitin-containing shell, incubating with sodium hypochlorite to remove organic contaminants, then removing the existing calcium carbonate using a 30 day dialysis against EDTA with sodium azide.

While the process is capable of providing a synthetic nacre-like product, it is expensive and time consuming, because it starts with a natural chitin template that must first be stripped of its natural mineralisation only to be replaced with synthetic mineralisation.

Most methods used seek to mineralise an artificially made organic template.

The alternative soaking method was developed in the late 1990s in Akashi's group (Taguchi, T, Kishida, A and Akashi, M. *Chem. Lett.*, 1998, 8, 711-712). In the alternate soaking method, a polymer template such as a chitosan film is repeatedly alternately soaked with solutions containing the respective cation and anion of the target material.

In the Kitano method, effusion of $CO_2$ gas from saturated $CO_2$-calcium carbonate solution increases the pH of the crystallisation solution leading to crystal nucleation and growth (Kitano, Y; Bull. *Chem. Soc. Jpn.*, 1962, 35(12), 1973-1980). However, the Kitano method tends to produce mineralisation at the peripheral surface of the polymer template only, so minimal penetration into the polymer matrix is achieved. Furthermore, the extent of mineralisation is limited due to the use of a saturated calcium carbonate solution.

The Kitano and alternate soaking methods can be combined by alternate soaking of the chitosan films with precursor calcium and carbonate solutions followed by treatment with saturated mineral solution (Munro, N H; Green, D W; Dangerfield, A; and McGrath, K M; *Dalton Trans.*, 2011, 40, 9259).

In the above methods, the template to be mineralised generally takes the form of a thin film. Although differently shaped templates can provide a range of differently shaped composite materials, the thickness of these materials is generally limited. Using a thicker template reduces mineralisation in the internal surfaces, leading to a weaker product. Therefore, while good mineralisation of an organic film can sometimes be achieved, growth is effectively limited to two dimensions. However, some attempts at making a genuinely three-dimensional material have been made.

Tang et al. formed an organic/inorganic composite material by depositing preformed inorganic crystals on an appropriately charged organic template (Tang, Z.; Kotov, N. A.; Magonov, S.; Ozturk, B., Nanostructured artificial nacre. *Nat. Mater.* 2003, 2(6), 413-418.). Growth in the third dimension (perpendicular to the largest surface) was achieved by depositing another organic layer on the top, then another layer of inorganic crystals i.e. "layer-by-layer" deposition.

Kato has also made advances in this area by forming the inorganic component in situ. Kato deposited a thin film of chitosan or chitin onto a glass substrate and grew calcium carbonate (the inorganic component) on top (Kato, T.; Suzuki, T.; Irie, T., Layered thin-film composite consisting of polymers and calcium carbonate: A novel organic/inorganic material with an organized structure. *Chem. Lett.* 2000, 2, 186-187). A layer of calcium carbonate of about 0.8 μm was achieved, using saturated calcium carbonate solution i.e. the "Kitano" method. Additional growth in the third dimension was achievable by deposition of another organic layer on top followed by more calcium carbonate deposition. The calcium carbonate was present as calcite.

While a large range of composite materials have been formed by mineralisation of a synthetic porous template, to date none of these materials demonstrate properties close to those seen in nacre. Mineralisation is generally limited to the periphery of the template with minimal mineralisation in the internal surfaces of the organic matrix. In addition, mineralisation tends to occur in two dimensions only. Where growth in the third dimension is achieved, it is via a laminar product built of alternate organic and inorganic layers. These layers are held together by weak intermolecular interactions, hence the material lacks the desirable structural factors of natural nacre.

Accordingly, it is an object of the invention to provide a method for producing mineralised composite materials, that goes at least some way towards overcoming the disadvantages of known methods, or to provide the public with a useful choice.

SUMMARY OF THE INVENTION

The invention relates generally to methods of forming ordered biomineral composites that incorporate the most significant design optimisations of nacre, such as highly ordered layers of mineral platelets and a viscoelastic chitin matrix to prevent fractures from spreading.

In one aspect the invention provides a method of forming a mineralised composite material comprising chitin and calcium carbonate, the method comprising:
(a) forming a permeable chitosan template from a chitosan solution,
(b) acetylating the chitosan template to form a permeable chitin template, and
(c) contacting the chitin template with calcium ions and carbonate ions under precipitation conditions, such that calcium carbonate mineralises on the peripheral and internal surfaces of the chitin template;
wherein mineralisation is carried out in the presence of (i) a soluble polymer containing one or more carboxylic acid groups and (ii) chitosan oligomers.

In another aspect the invention provides a method of forming a mineralised composite material comprising chitin and calcium carbonate, the method comprising contacting a permeable chitin template with calcium ions and carbonate ions under precipitation conditions, such that calcium carbonate mineralises on the peripheral and internal surfaces of the chitin template; wherein mineralisation is carried out in the presence of (i) a soluble polymer containing one or more carboxylic acid groups and (ii) chitosan oligomers.

In another aspect the invention provides a mineralised composite material formed from a method of the invention.

In another aspect the invention provides a mineralised composite material comprising calcium carbonate crystals incorporated on the peripheral and internal surfaces of a chitin template, wherein the composite material includes (i) a soluble polymer containing one or more carboxylic acid groups and (ii) chitosan oligomers, wherein the mineralised composite material is substantially homogenous in all directions when viewed at or above 100 μm resolution.

In the above aspects of the invention:

In one embodiment, the permeable chitin template is formed by acetylating a chitosan template. In one embodiment, the chitosan template is formed from a chitosan solution, preferably by drying a layer of chitosan solution. In one embodiment, the layer of chitosan solution is about 1 to 5 mm, preferably 2 to 4 mm deep. In one embodiment, the chitosan template is formed from an acidic aqueous solution of chitosan. In one embodiment, the acidic aqueous solution contains alcohol, preferably ethanol, 1-propanol 1,2-propandiol and 1,3-propandiol. In another embodiment, the acidic aqueous solution contains glycerophosphate. In one embodiment, the chitosan template is prepared in the presence of air bubbles to provide a chitosan foam.

In one embodiment the method of invention is carried out at ambient temperatures and pressures.

In one embodiment, the chitosan template is treated with base prior to acetylation to form a chitin template. In one embodiment, the chitin template is treated with base prior to mineralisation. Preferably the base is NaOH.

In one embodiment, the method of the invention includes soaking the permeable chitin template in two solutions—solution (i) which is a solution containing calcium ions through which $CO_{2(g)}$ has been bubbled, and solution (ii) which is a solution containing carbonate ions through which $CO_{2(g)}$ has been bubbled.

In one embodiment, the step of contacting a permeable chitin template with calcium ions and carbonate ions under precipitation conditions comprises:
(a) sequentially soaking the permeable chitin template in (i) a solution containing calcium ions through which $CO_{2(g)}$ has been bubbled and then in (ii) a solution containing carbonate ions through which $CO_{2(g)}$ has been bubbled,
(b) optionally repeating step (a) one or more times, preferably three to five times, and
(c) optionally soaking the permeable chitin template in a saturated $CaCO_3$ solution through which $CO_{2(g)}$ has been bubbled.

In another embodiment, the step of contacting a permeable chitin template with calcium ions and carbonate ions under precipitation conditions comprises:
(a) sequentially soaking the permeable chitin template in (ii) a solution containing carbonate ions through which $CO_{2(g)}$ has been bubbled and then in (i) a solution containing calcium ions through which $CO_{2(g)}$ has been bubbled,
(b) optionally repeating step (a) one or more times, preferably three to five times; and
(c) optionally soaking the permeable chitin template in a saturated $CaCO_3$ solution through which $CO_{2(g)}$ has been bubbled.

In one embodiment, solution (i) comprises 10 mM to 1 M calcium ions, preferably 300 mM to 1 M, more preferably 500 mM to 700 mM calcium ions.

In one embodiment, solution (ii) comprises 10 mM to 1 M carbonate ions, preferably 300 mM to 1 M, more preferably 500 mM to 700 mM carbonate ions.

In one embodiment one or both of solutions (i) and (ii) also comprise a soluble polymer containing one or more carboxylic acid groups. In one embodiment one or both of solutions (i) and (ii) comprise 0.5 to 10 wt %, preferably 1 to 5 wt %, more preferably 2 wt % soluble polymer containing one or more carboxylic acid groups, relative to the weight of the dried chitin template.

In one embodiment, the saturated $CaCO_3$ solution through which $CO_{2(g)}$ has been bubbled, comprises a soluble polymer containing one or more carboxylic acid groups. In one embodiment the saturated $CaCO_3$ solution through which $CO_{2(g)}$ has been bubbled comprises a 0.5 to 10 wt %, preferably 1 to 5 wt %, more preferably 2 wt % soluble polymer containing one or more carboxylic acid groups, relative to the weight of the dried chitin template.

In one embodiment one or both of solutions (i) and (ii) comprise chitosan oligomers. In one embodiment, one or both of solutions (i) and (ii) comprise about 5 to 50 wt %, preferably about 10 to 40 wt %, more preferably about 20 wt % chitosan oligomers relative to the weight of the dried chitin template.

In one embodiment, the saturated $CaCO_3$ solution through which $CO_{2(g)}$ has been bubbled, comprises chitosan oligomers. In another embodiment the saturated $CaCO_3$ solution through which $CO_{2(g)}$ has been bubbled comprises about 5 to 50 wt %, preferably about 10 to 40 wt %, more preferably about 20 wt %, chitosan oligomers relative to the weight of the dried chitin template.

In one embodiment, the soluble polymer containing one or more carboxylic acid groups comprises one carboxylic acid group per monomer. In another embodiment the soluble polymer containing one or more carboxylic acid groups comprises two carboxylic acid groups per monomer. In another embodiment the soluble polymer containing one or more carboxylic acid groups comprises carboxylic acid groups on about 5 to 100% of monomers, preferably about 20 to 100%, more preferably about 50 to 100% of monomers.

In one embodiment the soluble polymer containing one or more carboxylic acid groups is selected from the group comprising polyacrylic acid, polyaspartic acid, polylactic acid, polyglutamic acid, polymethacrylic acid, polyethylene glycol/polymethacrylic acid block co-polymers and mixtures thereof. Preferably, the soluble polymer comprises polyacrylic acid, polylactic acid, or a mixture of both.

In one embodiment the mineralised composite material comprises additional agents selected from the group comprising alginate, hyaluronate, and mixtures thereof.

In one embodiment the chitin template of the mineralised composite material is at least 20, 25, 30, 35, 40, 45, 50, 55, 60, 65, 70, 75, 80, 85, 90 or 95% mineralised. In one embodiment, the chitin template is at least 30 to 60%, more preferably 40-60% mineralised. In another embodiment, the chitin template is at least 60-90% mineralised, preferably 70-80% mineralised. Preferably, mineralisation is substantially homogenous across the peripheral and internal surfaces of the template.

In one embodiment, the calcium carbonate mineralises in the form of aragonite. In one embodiment, the calcium carbonate comprises at least 40, 50, 60, 70, 80, 90, 95 or 99% aragonite. Preferably, the calcium carbonate comprises 60 to 95%, more preferably 65 to 85% aragonite.

In one embodiment the calcium carbonate mineralises in the form of platelets.

Preferably, the platelets are about 1 to 20 μm diameter, more preferably about 1 to 15, most preferably about 1 to 10 μm diameter.

Preferably, the platelets are about 50 to 1000 nm depth, more preferably 50 to 800, more preferably 50 to 500 nm depth.

In one embodiment the aspect ratio of the platelets is about 5 to 400, more preferably 50 to 300, most preferably 100 to 300.

In one embodiment the shape of the platelets is selected from the group comprising hexagon, pentagon, polygon, rhombohedral, orthorhombic or mixtures thereof, preferably hexagon or pentagon.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

Embodiments of the invention will now be described with reference to the drawing in which.

DETAILED DESCRIPTION OF THE INVENTION

The invention provides a method of mineralising a chitin template at ambient temperature and pressure from an aqueous solution. The combination of the use of a chitin template, and the presence of both a soluble polymer containing one or more carboxyl groups, and chitin oligomers leads to the formation of a new hierarchical aragonite/chitin synthetic composite material.

Definitions

The term "precipitation conditions" as used herein with reference to calcium and carbonate ions refers to the situation where the activity product of the calcium and carbonate ions is greater than the solubility product of the calcium carbonate salt, at least in parts of the solution in contact with nucleation sites. Under these conditions the solution is supersaturated and the insoluble salt will precipitate out of solution. Where solutions of calcium ions and carbonate ions are combined, precipitation conditions occur when the combined solution is in the correct pH range. For solutions that have had $CO_{2(g)}$ bubbled through them, precipitation conditions will be achieved when sufficient $CO_{2(g)}$ diffuses from the solution, raising the pH.

As used herein the terms "chitin" and "chitosan" unless otherwise stated, refer to a linear co-polymer of β-(1,4) linked D-glucosamine and N-acetyl-D-glucosamine. Where the number of N-acetyl-D-glucosamine units is greater than 50%, the co-polymer is generally termed chitin. Where the number of acetyl-D-glucosamine units is lower than 50%, the co-polymer is generally termed chitosan. Chitosan can be produced by deacetylation of chitin. Commercially available chitosan typically has a degree of deacetylation of between about 50 to 100%. Both α- and β-chitosan are suitable for use in the invention. The degree of deacetylation (% DD) of chitin/chitosan influences its solubility and other properties.

As used herein the term "chitosan oligomer" unless otherwise stated, refers to a chitosan molecule of about 10 to 50 monomer units.

As used herein the term "permeable chitosan template" unless otherwise stated, refers to a material made of chitosan able to separate two solutions of different ion compositions, being permeable so as to allow certain molecules to pass through, thereby allowing the two solutions to mix within the internal structure of the template. Permeability arises as a consequence of interconnecting pores and channels that allow movement of ions throughout the template, including, when the template is a membrane, from one side of the template to the other. The permeable chitosan template comprises peripheral surfaces and internal surfaces. The peripheral surfaces are those on the exterior of the template while the internal surfaces are the surfaces of the pores and channels within the template. The "permeable chitin matrix" is of the same shape and morphology as the permeable chitosan template from which it is prepared. For example, both the permeable chitosan and chitin templates may comprise films, membranes, capsules, balls, beads or threads. A chitin template for mineralisation in a method of the invention might typically be a film of 20 to 100 µm thickness.

As used herein the term "mineralise" unless otherwise stated, refers to the process by which a solution of a calcium carbonate salt solidifies and crystallises. In the process of mineralisation the salt solidifies and crystallises on a surface of the chitin template at an available nucleation site. The percentage of mineralisation relates to the relative weight of the calcium carbonate deposits in the final composite material. The percentage of mineralisation can be calculated by comparing the weight of the mineralised template with the weight of the original dried chitin template. Other organic materials such as chitosan oligomers will be incorporated into the composite material but are of relatively negligible weight.

Mineralisation can range from completely homogenous, where the crystals of insoluble salt are completely evenly distributed on the available nucleation sites of the chitin template, including both the peripheral and internal surface; to heterogenous, where some surfaces of the template are heavily mineralised and others are non-mineralised. Preferably, mineralisation is substantially homogenous in the method of the invention. Homogeneity can be assessed with reference to the resolution at which a surface of the material has discernable features.

The term "platelet" as used herein refers to a crystalline structure that grows or has grown preferentially in the lateral direction relative to the perpendicular direction with reference to a surface of the chitin template. Consequently, the width of a platelet will exceed its depth such that the aspect ratio of the platelet is above 1.0. In theory, platelets are not limited to a particular size but tend to remain relatively small because preferential lateral growth means that they meet neighbouring platelets on the same surface area relatively quickly, and are therefore forced to stop growing laterally.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Forming a Permeable Chitin Template from a Chitosan Solution

Chitosan is derived from animal chitin by removal of acetyl groups from a high percentage of glucose units making up the polymer chains. Chitin constitutes a major industrial waste product from the fishing industry, so is highly abundant. Chitosan is biocompatible, antibacterial and environmentally benign, making it ideal for pharmaceutical and medical applications.

A chitosan solution for use in the methods of the invention can be prepared as described in the Example 1. Typically, acetic acid is used to help dissolve the chitosan in water. As described above, chitosan has a degree of deacetylation of above 50%. Typically, chitosan for use in the methods of the invention has a degree of deacetylation of about 80%.

In one embodiment the chitosan solution comprises chitosan of 50,000-500,000 Da.

In one embodiment the chitosan solution comprises chitosan of about 50,000-190,000 Da. In one embodiment, the chitosan solution comprises chitosan of about 100,000-300,000 Da. In another embodiment the chitosan solution comprises chitosan of about 390,000-500,000 Da.

In one embodiment the chitosan solution comprises about 0.1 to about 5 wt % chitosan, preferably 0.2 to 5 wt %, more preferably 1 to 5 wt %.

Solutions of increased chitosan concentrations correlate with increased toughness and stiffness in the final dried template and increased toughness in hydrated chitosan templates. Chitosan templates prepared from solutions of 0.16-5 wt % chitosan can be handled by hand or with forceps without tearing. Typically, films are produced using 2 wt % chitosan.

The chitosan solution may be made using only water, or can comprise other agents such as acetic acid, methanol, ethanol, maleic acid, 1-propanol, 2-propanol, 1,2-propanediol, 1,3-propanediol and glycerophosphate which can affect the properties of the resulting chitin template. The physical structure of the organic template can be altered by changing the solvent in which the chitosan is dissolved. In one embodiment, chitosan is dissolved in water with acetic acid. Removal of the solvent leaves a chitosan film. Adding a co-solvent such as 1-propanol, 2-propanol, 1,2-propandiol or 1,3-propandiol to the chitosan dissolved in acetic acid solution allows the chitosan to stay in solution. This gives the resulting film different mechanical and physical properties For example, including one of ethanol, propanol, 1,2-propandiol or 1,3-propandiol as a cosolvent makes the resulting films more flexible, with the amount of flexibility increasing with increasing amounts of one of these cosolvents. The increase in flexibility for templates prepared with propandiol as a cosolvent is more pronounced than for ethanol or propanol.

The fracture propagation is also altered by adding a cosolvent, with easier propagation of tears in templates prepared with one of the colsolvents ethanol, propanol, 1,2-propandiol or 1,3-propandiol, than in templates prepared with no cosolvent.

The chitosan template may comprise a membrane or film but may also be differently shaped. The chitosan solution can be made to form a template of any shape by using moulds. In Example 1, the solution is poured into a Petri dish until 2-3 mm thick, and dried at 50° C. The dried solution forms a permeable chitosan template in the form of a film that is suitable for mineralisation after acetylation.

While a basic mould such as is formed by a Petri dish will provide a permeable chitosan template in the form of a membrane, other moulds can be used to obtain templates with other shapes or to introduce microscopic or macroscopic structural details into the template. For example, capsules of permeable chitosan can be prepared, acetylated and mineralised. Such capsules are likely to be of use in filling bone voids caused by trauma and disease. Capsule templates can also be used as vehicles for delivering pharmaceuticals, therapeutics and the like. Irrespective of the shape of the mould, the chitosan solution should generally be about 2-3 mm thick. Heating of this chitosan solution ensures the complete evaporation of the solvent and the acid used to dissolve the chitosan polymer to make the solution. After drying, complete separation of the template from the mould is possible. Permanent cross-linkers are not required to reduce processing time, which ensures that potentially toxic components are not introduced into this structural biomaterial.

Separation is best achieved if plastic moulds are used, due to the mismatch in the electrostatic charges of the two substrates. Preferably, chitosan templates are generated in the form of membranes with thicknesses between 20-100 µm, regulated by the volume of chitosan solution used. Once the permeable chitosan template has formed from the chitosan solution, it is acetylated. Any standard method of acetylation can be used, for example, by soaking the template in an acetylating agent such as acetic anhydride as described in Example 1. Once acetylated, the template is comprised of chitin. The degree of deacetylation may be about 30 to 50%.

As in the chitosan template, the permeable chitin template comprises pores which allow movement of fluid through the matrix. The pores can partially transverse the matrix or can be distributed through an entire region of the chitosan template including a surface thereof. The pores can be interconnected so as to form a continuous flow path or channels throughout the matrix of the template. In one embodiment the chitin template is sponge-like, comprising a plurality of continuous and interconnected pores.

The pores and channels may vary in size and may be more or less homogenous or heterogeneous in size. Pores and channels of different length scales may be present simultaneously. For example, the template may contain voids and channels that are on both the macroscopic (1000 µm) and microscopic (10-100 µun) level. Large pores and channels may be introduced into the chitosan template using a mould to prevent chitosan solution setting in some spaces. Smaller pores and channels arise naturally when the chitosan solutions set to form the template. The sizes of the pores and channels can be controlled by varying factors such as the concentration of chitosan used to make the template and other additives present. High concentrations of chitosan will create templates with a high degree of entanglement between the polymer chains. Greater entanglement causes the pores and channels between the polymers to be smaller.

Including an additive like glycerophosphate induces larger pores and channels into the template, as well as the small pores which naturally occur. This hierarchical structure allows pores of multiple sizes spanning a number of length scales to exist within one template and can lead to enhanced permeability of the template.

Techniques of preparing the template can also influence the size of the pores and channels.

Deliberately adding air bubbles into the chitosan template gives pores of various sizes in chitosan foams. Preparing the chitosan foam with a controlled air flow can produce chitosan foams with close to monodisperse pore sizes, where the pore sizes are tuneable by selecting the correct experimental methods. Such methods are readily understood by persons skilled in the art.

Once acetylated, the chitin template will have the same basic pattern of pores and channels as the chitosan template.

Before mineralisation either the chitin or chitosan template can be treated with a base such as sodium hydroxide to increase its firmness. This is an optional step. Typically, a 1 M aqueous NaOH solution is used to coagulate (set or cure) the template. The resulting template is tougher, less flexible, more difficult to tear, and is more stable for prolonged periods in water. Aqueous NaOH solutions with molar concentrations of 2-5 M can also be used and provide increasingly toughened membranes. Other basic solutions can be used, such as KOH in aqueous solution or NaOH or KOH in ethanol or methanol solutions, or a combination thereof.

Mineralisation of the Chitin Template

In the methods of the invention the chitin template is mineralised by contacting it with the cation (calcium ion) and anion (carbonate ion) under precipitation conditions. Precipitation conditions are conditions under which the cation and anion present in the solution will precipitate, as defined above. The concentration of calcium and carbonate ions must be sufficiently high so as to form a supersaturated solution at the pH of the solution. Initially, the calcium and carbonate solutions may be contacted with the chitin template under non-precipitation conditions, provided that precipitation conditions are achieved, for example, by raising the pH of the solution.

The chitin template can be contacted with the calcium and carbonate ions using any means known in the art. For example, the ammonium carbonate diffusion method and double diffusion methods previously discussed can be used, in addition to the other methods described in the Examples.

In one embodiment, the Kitano method is used to contact the permeable chitin template with the calcium and carbonate ions. The Kitano crystallisation solution comprises calcium carbonate dissolved in a solution of water through which $CO_{2(g)}$ has been bubbled. The $CO_2$ acidifies the solution so that the calcium carbonate stays in solution. The solution is then contacted with the chitin template. As the $CO_2$ diffuses from the solution, the pH of the solution rises until precipitation conditions are achieved. The calcium carbonate then begins to precipitate at the nucleation sites.

In another embodiment, the alternate soaking method is used. The alternate soaking process comprises sequential soaking of the chitin templates in separate $CaCl_2$ and $NaHCO_3$ solutions previously bubbled with $CO_{2(g)}$. Soaking is generally for at least about an hour, although soaking can occur for up to about 24 hours. The alternate soaking process is believed to increase nucleation at internal surfaces of the chitin matrix in addition to nucleation at the peripheral surfaces. Generally, the chitin templates will be sequentially soaked in each solution about three to five times.

In another embodiment, the Kitano and alternative soaking methods are combined, for example, by alternate soaking of the chitin template with individual solutions of calcium ions and carbonate ions, followed by treatment with saturated calcium carbonate solution. (Munro, N H; Green, D W; Dangerfield, A; and McGrath, K M; *Dalton Trans.*, 2011, 40, 9259). Again, each solution can be left to soak for an hour, or up to 24 hours.

Example 1 describes using the alternate soaking and Kitano methods to mineralise a permeable chitin template. In the methods of the invention, either technique can be used separately, or both can be combined, as in Example 1.

In one embodiment, the step of contacting the permeable chitin template with calcium ions and carbonate ions under precipitation conditions comprises:
(a) sequentially soaking the permeable chitin template in
(i) a solution containing calcium ions through which $CO_{2(g)}$ has been bubbled; and (ii) a solution containing carbonate ions through which $CO_{2(g)}$ has been bubbled, wherein soaking the permeable chitin template in one solution followed by the other solution constitutes a cycle and wherein between one and fifty cycles are carried out, preferably three to 10 cycles, more preferably five cycles.

In industrial situations, the templates may be attached to a frame which is suspended in a solution. The used solution may be drained out of the bottom of the vessel holding the solution, and can be replaced with fresh solution from the top of the vessel. Alternatively, the frames could be raised out of each solution and then lowered into the other solution.

During the process of mineralisation the chitin template changes from translucent to a milky white colour. The wet mineralised composite material also becomes more rubbery and elastic as mineralisation progresses.

In methods of the invention, additives such as a soluble polymer containing one or more carboxylic acid groups, and chitosan oligomers, are incorporated into the mineralised composite material.

Each of these components can also be added to one or both of the soaking solutions of $CaCl_2$ and $NaHCO_3$, if the alternate soaking process is to be used. If the Kitano method is to be used, each of the additives can be included in the Kitano solution. If both the alternate soaking and Kitano methods are to be used, each additive can be added to any of the solutions used in the mineralisation process.

The chitosan oligomers and soluble polymer containing one or more carboxylic acid groups can be added to the mineralisation solution in any order, or at any stage of the mineralisation process. However, best results may be achieved by adding the solution of chitosan oligomers to the mineralisation solution which already contains the soluble polymer containing one or more carboxylic acid groups. In particular, best results are achieved by contacting the soluble polymer-containing mineralisation solution with the chitin template for approximately 30 minutes before adding the chitosan oligomers.

In Example 1, the soluble polymer containing one or more carboxyl groups was added to soaking solutions of $CaCl_2$ and $NaHCO_3$. The chitosan oligomers were dissolved in water and added to the Kitano mineralisation solution.

The soluble polymer containing one or more carboxylic acid groups will generally have a molecular weight of at least 500 g/mol, more preferably about 1800 g/mol. This component acts as a crystal inhibitor in solution but when absorbed onto the surface of the organic template, acts as a nucleator. Its incorporation in the mineralisation procedure leads to larger crystals and more mineralisation in the form of aragonite.

The soluble polymer containing one or more carboxylic acid groups includes proteins.

In one embodiment the amount of soluble polymer containing one or more carboxylic acid groups in each solution in which it is present is 0.5 wt % to 10 wt % relative to the weight of the dried chitin template. Preferably, the amount is 1 wt % to 5 wt %, more preferably 2 wt %. The actual concentration of the soluble polymer is not important, provided the polymer remains in solution. The relevant property is the ratio of the amount of soluble polymer to the amount of chitin template when measured in its dried state.

For example, if a chitin template is prepared using 0.4 g chitosan, 20 mL of a solution comprising 2 wt % soluble polymer containing one or more carboxylic acid groups relative to the weight of the dried chitin template will have a concentration of 0.267 mg mL$^{-1}$ of soluble polymer.

Solutions that are much higher or lower concentration can be used, provided the ratio of soluble polymer to dried chitin template is in the appropriate range.

The soluble polymer must contain at least one carboxylic acid group per molecule but will generally contain many more, such as carboxylic acid groups on 5 to 100% of monomers. In one embodiment, the soluble polymer will contain at least one carboxylic acid group per monomer.

Soluble polymers containing one or more carboxyl groups can be selected from the group comprising polyacrylic acid, polyaspartic acid, polylactic acid, polyglutamic acid, polymethacrylic acid, polythylene glycol/polymethacrylic acid block co-polymers and the like.

In one embodiment, the soluble polymer containing one or more carboxyl groups comprises polyacrylic acid, polylactic acid, or a mixture of both. Preferably, the soluble polymer containing one or more carboxyl groups comprises polyacrylic acid.

The molecular weight of the soluble polymer containing one or more carboxylic acid groups can be varied with corresponding changes in the concentration of the other additives.

The chitosan oligomers are incorporated into the growing composite material, as indicated by a number of changes. For example, the chitosan oligomer solution in contact with the chitin template changes from yellow to clear and colourless, as the oligomers are incorporated. The material produced also becomes thicker, as the chitosan oligomers induce three-dimensional growth via a self-assembly process.

Mineralisation is preferably in the form of platelets. Aragonite and calcite are polymorphs of calcium carbonate, each having different crystal symmetries and consequently, different properties.

Aragonite is harder and denser than calcite. In the methods of the invention, mineralisation generates aragonite preferentially.

In one embodiment, the invention provides a method of forming a mineralised composite material comprising chitin and calcium carbonate, the method comprising
(a) soaking a chitin template in calcium chloride, sodium bicarbonate and optionally saturated calcium carbonate solutions, through each of which $CO_{2(g)}$ has been bubbled, and one or more of which contains polyacrylic acid, and
(b) adding chitosan oligomers to the mixture formed in step (a) to form a composite material comprising chitin and calcium carbonate.

In one embodiment the calcium carbonate is substantially in the form of aragonite.

The Mineralised Composite Material

The method of the invention produces a mineralised composite material that demonstrates many of the properties of nacre. The mineralised composite material comprises calcium carbonate crystals incorporated on the peripheral and internal surfaces of a chitin template. The composite material includes a soluble polymer containing one or more carboxylic acid groups and chitin oligomers, wherein the mineralised composite material is substantially homogenous in all directions when viewed at or above 100 μm resolution.

The methods of the invention cause an intimate association between the organic and inorganic components of the composite material in all three dimensions. In the mineralised composite material of the invention, the inorganic phase is uniformly distributed throughout the organic phase, and vice versa. Consequently, the composite material comprises organic and inorganic components that appear visibly homogenous at or above about 100 μm resolution. This means that light is uniformly scattered on this length scale such that individual features of organic vs inorganic layers cannot be distinguished. To the naked eye or when viewed through a microscope at 100 μm resolution or greater the material appears substantially homogenous.

This contrasts with previously known materials produced by a discontinuous layer-by-layer method, where bands of organic and inorganic layers are clearly visible at 100 μm resolution.

Figure 1:
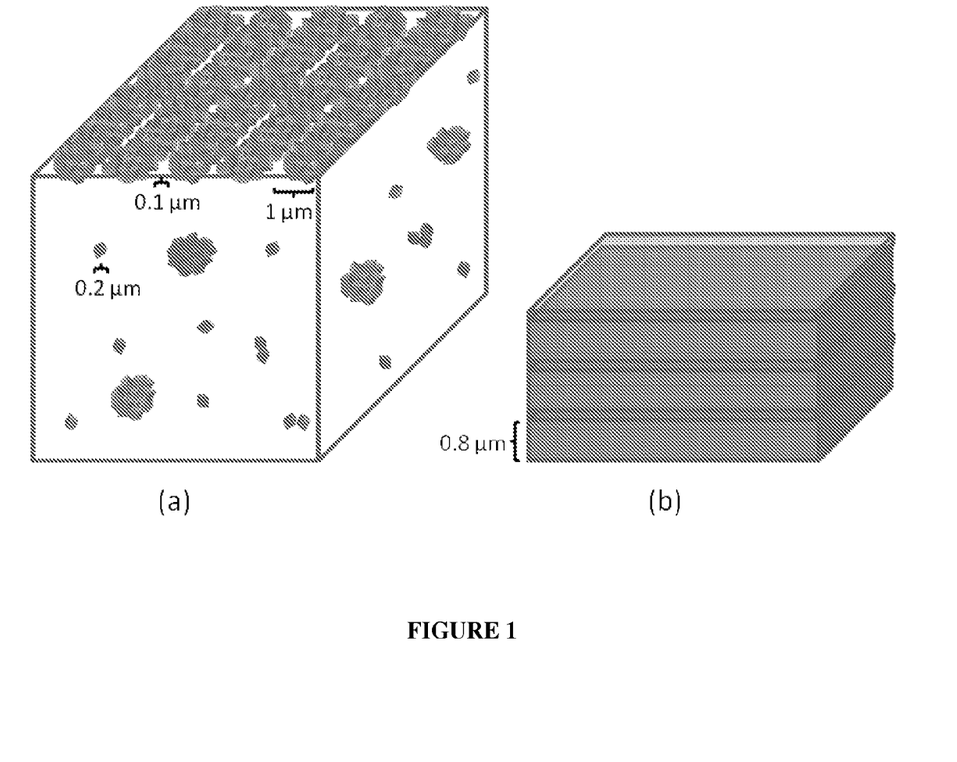
FIG. 1 is a schematic of the composite structure of (a) the mineralised composite material of the invention and (b) a known nacre-like composite material (not to scale). The composite of the invention has both organic and inorganic components when measured in all three directions; the other composite is layered in one direction and has only one component in the other two directions measured.
Figure 2:
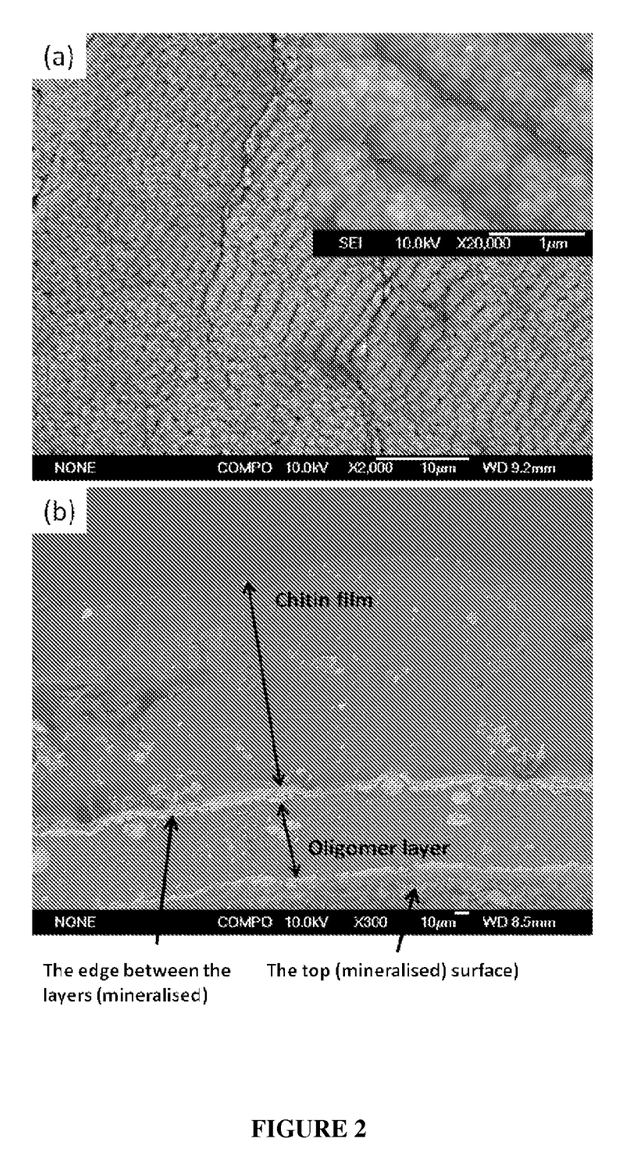
FIG. 2 shows SEM images of chitin/aragonite/polyacrylic acid/chitosan oligomer composite materials showing (a) the top surface of the composite and (b) the cross-section of the composite (similar to FIG. 1a). The inset in FIG. 2a is in normal SEM imaging mode; the main figures are in backscatter mode where heavier elements show up as lighter colours.
Figure 3:
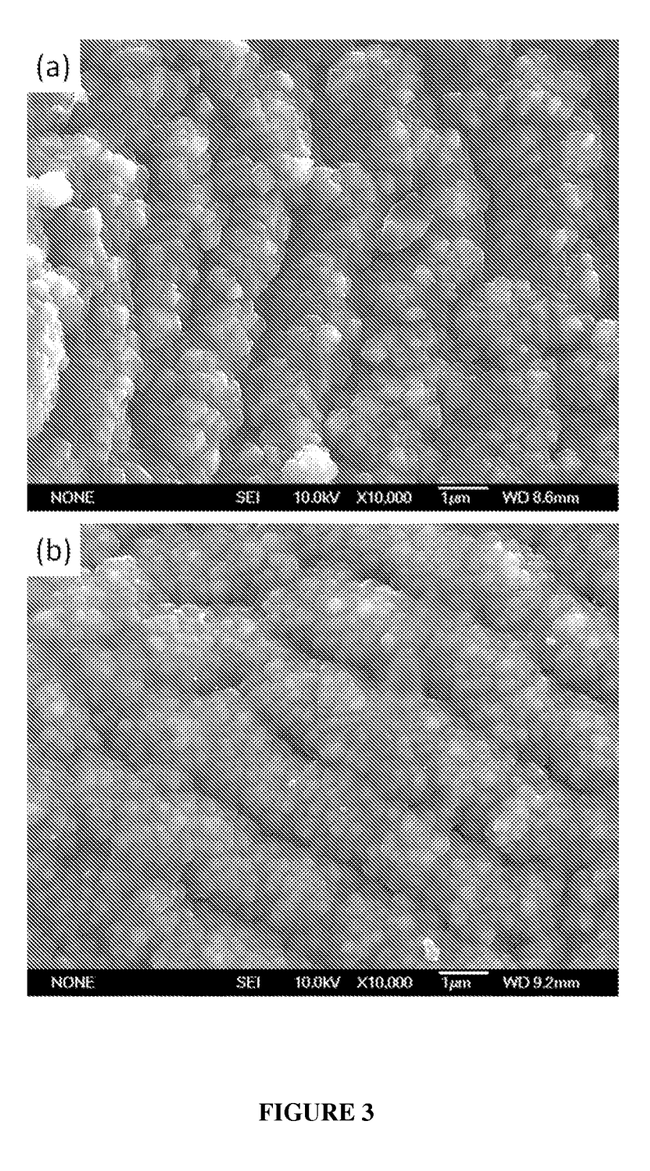
FIG. 3 shows SEM images of chitin/aragonite/polyacrylic acid composite materials (a) prepared without oligomers present and b) prepared with oligomers present (similar to FIG. 1a). The similar appearance of the two materials shows that the presence of the oligomers does not significantly alter the growth of the composite materials but rather induces three dimensional growth. The crystals appear less defined in (b) due to the oligomers "gluing" the crystals together.
Figure 4:
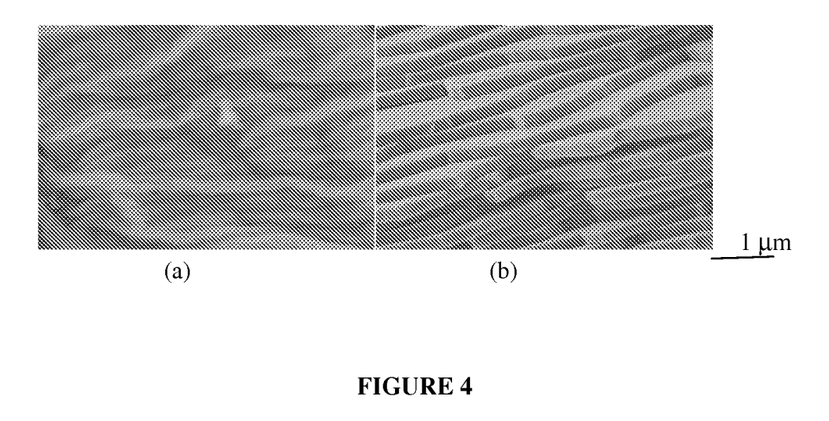
FIG. 4(a) shows an SEM image in backscatter mode of a base-treated chitin/polyacrylic acid/aragonite composite material of the invention. Heavier elements show up as lighter colours. The image shows "platelet"-like crystals in stacks (similar to (b) nacre, same magnification, SEM image in scanning electron mode).

The inorganic crystal growth occurs laterally along interior and exterior surfaces of the organic chitin template. Inorganic crystals (cuboids) approximately 100 to 300 nm in size, aggregate into larger mesocrystals. At the peripheral surface of the organic template, these cuboids are seen to aggregate into structures, each structure having a thickness of 1 to 2 μm. The structures are spaced approximately 100 nm apart, as can be seen in FIG. 1(a).

By promoting mineralisation on the internal surfaces of the template, the structure of the composite material of the invention more closely resembles nacre than known nacre-like materials. The composite material of the invention also comprises platelets of similar sizes, aspect ratios and shapes to those found in nacre. As such, the composite materials of the invention share many of the advantageous properties of nacre.

In one embodiment the chitin template of the mineralised composite material is at least 20, 25, 30, 35, 40, 45, 50, 55 or 60% mineralised. Preferably, the chitin template is at least 30 to 60%, more preferably 40-60% mineralised. Preferably, mineralisation is substantially homogenous across the peripheral and internal surfaces of the template.

The degree of mineralisation can be assessed by inspection using a compound light microscope, or an electron microscope. The composite material of the invention can be sliced open to expose its interior. Visual inspection aided by microscopy allows the person skilled in the art to assess the degree of mineralisation and homogeneity.

In addition to the degree of mineralisation, the type of crystallisation of the polymorphic structure, can be assessed. The width, depth and aspect ratio of the platelets formed can also be determined.

EXAMPLES

Example 1

Chitin Templates

Chitosan (CS, 0.400 g) was stirred in 19.8 mL $H_2O$, acetic acid (0.200 mL) was added and the mixture was stirred for 1 h. The 2% (wt/wt) CS solution in 1% (v/v) acetic acid solution (20 mL) was centrifuged at 3,000 rpm for 20 mM, poured into a circular 9 cm diameter plastic Petri dish and dried at 50° C. for 48 h. Different concentrations of chitosan produce solutions of different viscosities. Acetic anhydride (5.0 mL) dissolved in methanol (25 mL) was applied to the chitosan template and left overnight at ambient temperature. The acetylated film was rinsed with ethanol and washed thoroughly with water.

Mineralisation

The chitin matrix was mineralised by the sequential soaking of the films in 30 mL aliquots of calcium chloride (500 mM), sodium bicarbonate (500 mM) and saturated calcium carbonate solutions, respectively. The films were soaked in $CaCl_2$ and $NaHCO_3$ solutions for 24 h and in the saturated calcium carbonate solution for five days. Polyacrylic acid (0.008 g) was dissolved in each of the solutions.

$CaCl_2$ and $NaHCO_3$ solutions were bubbled with $CO_{2(g)}$ for 1 h prior to use. A saturated calcium carbonate solution (the mineralisation solution) was prepared following the procedure outlined by Kitano (Kitano Y., The behaviour of various inorganic ions in the separation of calcium carbonate from a bicarbonate solution. *Bull. Chem. Soc. Jpn.* 1962, 35(12), 1973-1980).

A 1 M aqueous NaOH solution can be used to coagulate (set or cure) the template prior to the pre-soaking steps for 1 hour. Aqueous NaOH solutions with molar concentrations of 2-5 M can also be used and provide increasingly toughened membranes.

The Kitano crystallisation solution is made by mixing 2.6 g of calcium carbonate (precipitated calcium carbonate-Albafil A-2-324-12) with 1 L of distilled MilliQ water and bubbling through $CO_2$ for 6 hours at a rate of 3 L/hour. The solution is then double filtered to remove un-dissolved crystals. Carbon dioxide is bubbled through the solution for a second time for 30 minutes at a rate of 3 L/hour. High saturation levels of carbon dioxide, maintained in all solutions and imbibed into chitosan templates, is significant for driving carbonate formation.

The oligomers (chitosan oligomers, 20 wt % with respect to the chitin template) were dissolved in water (typically about 2-5 mL) and this solution was added to the Kitano solution 30 minutes after the Kitano solution was added to the chitin template. The saturated calcium carbonate solution which contained both the poly(acrylic acid) polymer and the chitosan oligomers led to the formation of a precipitate. The presence of both the poly(acrylic acid) polymer and the chitosan oligomers in the respective calcium chloride and the sodium bicarbonate solutions was not a problem and no precipitate formed.

Materials

Chitosan (CS, degree of deacetylation=82±2%, $M_w$=100,000-300,000 g mol$^{-1}$, Acros Organics), $CaCl_2 \cdot 2H_2O$ (Sigma-Aldrich, ACS reagent), $NaHCO_3$ (Panreac, AR grade), $CaCO_3$ (Univar, AR grade), PAA (Sigma-Aldrich, average $M_w=1,800$ g mol$^{-1}$), acetic acid (Univar, AR grade), acetic anhydride (AR grade, Acros Organics) and methanol (LR grade) were used as received. Deionised water (18.2 MΩcm resistivity, Sartorius arium 611UV purification system) was used in all solutions.

Characterisation

The chitosan and reacetylated chitin films were characterised by FT-IR spectroscopy. The powdered samples were prepared as KBr discs and the spectra were acquired from five scans with 4 cm$^{-1}$ resolution on a Perkin-Elmer Spectrum One Ft-IR Spectrometer. The degree of deacetylation (DD) was calculated using the method of Brugnerotto (Brugnerotto, J.; Lizardi, J.; Goycoolea, F. M.; Argüelles-Monal, W.; Desbrières, J.; Rinaudo, M., An infrared investigation in relation with chitin and chitosan characterization. Polymer 2001, 42 (8), 3569-3580). The mineralised films were characterised by SEM, EDS, powder XRD and microRaman spectroscopy. SEM samples were mounted on aluminium stubs with double sided carbon tape. Cross-sectional samples were prepared by mounting a piece of the sample against a carbon-tape coated cut stub, with the sample protruding above the top of the stub. A folded over piece of carbon tape was applied, level to the top of the stub. A second piece of carbon tape was pressed onto the tape and the sample. The whole stub was frozen in liquid nitrogen, and the tape and sample were fractured while frozen, then thawed. The samples were coated with two coats of carbon using a Quorum Q150T coater. SEM images were acquired using a JEOL JSM-6500F field emission SEM in SEI and BEI mode. An accelerating voltage of 10.00 kV and a probe current of 9.0 μA were typically used. The instrument was generally operated at a working distance of approximately 10 mm. EDS imaging was carried out in BEI mode, with an accelerating voltage of 15.0 kV and a probe current of 17 μA. Samples were prepared for powder X-ray diffraction (XRD) by grinding of the composites in liquid nitrogen to form a powder. XRD patterns were acquired with a PANalytical X'Pert Pro powder difffractometer using Cu/Kα radiation. The data were obtained with generator settings of 45 kV and 40 mA, and scans were acquired with 2θ from 5 to 80°. The diffraction patterns were compared to diffraction patterns of known compounds from the database, using the software X'Pert Highscore 2.2c. Calculations of the various amounts of the three anhydrous polymorphs of calcium carbonate were performed using the software or from the peak areas for the peaks at 25.0° (vaterite), 29.5° (calcite) and 45.9° (aragonite) as detailed elsewhere (Dickinson, S. R.; McGrath, K. M., Quantitative determination of binary and tertiary calcium carbonate mixtures using powder X-ray diffraction. Analyst 2001, 126 (7), 1118-1121). Raman spectra of individual crystals were obtained using a Renishaw RM2000 ramascope using 633 nm excitation with a circularly polarized laser and a Renishaw edge-laser filter. A linear polarizer was not used. The incident laser beam of a Jobin-Yvon LabRam spectrometer was centred on a crystal and spectra were taken using a 633 nm HeNe laser centred at 800 cm$^{-1}$, with the pinhole set at 1000 μm. A beam intensity of 3 mW and a $N_2(1)$ cooled CCD were used. The spectrometer was calibrated using a silicon standard, setting the major peak to 520.5 cm$^{-1}$.

Industrial Applicability

The methods of the invention can be used to produce a material for use in a variety of industries including as a coating for medical devices such as needles or syringes, as a material for bone and/or dental implants, and in paints and other surface protection compositions.

For example, the material of the invention may be used as a substitute for toxic anti-fouling coatings for sea water proofed objects such as boat hulls. When applied to surfaces subject to contamination such as buildings and boat hulls, the layered structure of the material allows it to be stripped back by treatment with acetic acid, to provide a new clean smooth surface.

The strong, yet non-brittle properties of the material of the invention also make it suitable as a ceramic or construction material, in for example, the automobile, aircraft or building industries.

The composite materials of the invention may demonstrate equivalent biomechanical properties to those of nacre and may constitute stronger, more resilient bioactive mineral coatings for medical implants. The invention can also be extended to fabricate mineralised filler particles. There is a current unmet need for high performance synthetic bioceramics for hard tissue replacement. Coatings that simulate nacre will improve biomechanical support of biomedical implants in calcified tissues. The use of bioceramics and the ability to incorporate functional proteins and enzymes into the biocomposite structure will promote bio-integration and promote regeneration processes.

The invention claimed is:

1. A method of forming a mineralised composite material comprising chitin and calcium carbonate, the method comprising:
    (a) forming a permeable chitosan template from a chitosan solution;
    (b) acetylating the permeable chitosan template to form a permeable chitin template; and
    (c) contacting the chitin template with calcium ions and carbonate ions under precipitation conditions, such that calcium carbonate mineralises on peripheral and internal surfaces of the permeable chitin template;
    wherein mineralisation is carried out in the presence of (i) a soluble polymer containing one or more carboxylic acid groups and (ii) chitosan oligomers.

2. A method of forming a mineralised composite material comprising chitin and calcium carbonate, the method comprising contacting a permeable chitin template with calcium ions and carbonate ions under precipitation conditions, such that calcium carbonate mineralises on peripheral and internal surfaces of the chitin template; wherein mineralisation is carried out in the presence of (i) a soluble polymer containing one or more carboxylic acid groups and (ii) chitosan oligomers.

3. The method of claim 2 wherein the permeable chitin template is formed by acetylating a chitosan template.

4. The method of claim 1 wherein the step of contacting the permeable chitin template with calcium ions and carbonate ions under precipitation conditions comprises:
    (a) sequentially soaking the permeable chitin template in (i) a solution containing calcium ions through which $CO_2(g)$ has been bubbled, and then in (ii) a solution containing carbonate ions through which $CO_2(g)$ has been bubbled;
    (b) repeating step (a) zero, one, three to five or more times; and
    (c) optionally soaking the permeable chitin template in a saturated $CaCO_3$ solution through which $CO_{2(g)}$ has been bubbled.

5. The method of claim 2 wherein the step of contacting the permeable chitin template with calcium ions and carbonate ions under precipitation conditions comprises:
    (a) sequentially soaking the permeable chitin template in (i) a solution containing carbonate ions through which $CO_{2(g)}$ has been bubbled, and then in (ii) a solution containing calcium ions through which $CO_{2(g)}$ has been bubbled;

(b) repeating step (a) zero, one, three to five or more times; and (c) optionally soaking the permeable chitin template in a saturated $CaCO_3$ solution through which $CO_{2(g)}$ has been bubbled.

6. The method of claim 4 wherein one or both of (i) the solution containing calcium ions through which $CO_2(g)$ has been bubbled, and (ii) the solution containing carbonate ions through which $CO_2(g)$ has been bubbled, further comprises 0.5 to 10 wt % of the soluble polymer containing one or more carboxylic acid groups, relative to dry weight of the permeable chitin template.

7. The method of claim 5 wherein one or both of (i) the solution containing carbonate ions through which $CO_2(g)$ has been bubbled, and (ii) the solution containing calcium ions through which $CO_2(g)$ has been bubbled, further comprises 0.5 to 10 wt % of the soluble polymer containing one or more carboxylic acid groups, relative to dry weight of the permeable chitin template.

8. The method of claim 1 wherein the soluble polymer containing one or more carboxylic acid groups is present in a saturated $CaCO_3$ solution through which $CO_{2(g)}$ has been bubbled.

9. The method of claim 8 wherein the saturated $CaCO_3$ solution through which $CO_{2(g)}$ has been bubbled comprises 0.5 to 10 wt % of the soluble polymer containing one or more carboxylic acid groups, relative to dry weight of the permeable chitin template.

10. The method of claim 4 wherein one or both of (i) the solution containing calcium ions through which $CO_2(g)$ has been bubbled, and (ii) the solution containing carbonate ions through which $CO_2(g)$ has been bubbled, further comprises about 5 to 50 wt % chitosan oligomers, relative to dry weight of the permeable chitin template.

11. The method of claim 5 wherein one or both of (i) the solution containing carbonate ions through which $CO_2(g)$ has been bubbled, and (ii) the solution containing calcium ions through which $CO_2(g)$ has been bubbled, further comprises about 5 to 50 wt % chitosan oligomers, relative to dry weight of the permeable chitin template.

12. The method of claim 4 wherein the saturated $CaCO_3$ solution through which $CO_{2(g)}$ has been bubbled comprises about 5 to 50 wt % chitosan oligomers, relative to dry weight of the permeable chitin template.

13. The method of claim 5 wherein the saturated $CaCO_3$ solution through which $CO_{2(g)}$ has been bubbled comprises about 5 to 50 wt % chitosan oligomers, relative to dry weight of the permeable chitin template.

14. The method of claim 1 wherein the soluble polymer containing one or more carboxylic acid groups comprises carboxylic acid groups on about 5 to 100% of monomers.

15. The method of claim 1 wherein the soluble polymer containing one or more carboxylic acid groups is selected from the group consisting of polyacrylic acid, polyaspartic acid, polylactic acid, polyglutamic acid, polymethacrylic acid, polyethylene glycol/polymethacrylic acid block co-polymers and mixtures thereof.

16. A mineralised composite material comprising calcium carbonate crystals incorporated on peripheral and internal surfaces of a chitin template, wherein the composite material includes (i) a soluble polymer containing one or more carboxylic acid groups and (ii) chitosan oligomers, wherein the mineralised composite material is substantially homogenous in all directions when viewed at or above 100 μm resolution.

17. The mineralised composite material of claim 16 which comprises additional agents selected from the group consisting of alginate, hyaluronate and mixtures thereof.

18. The mineralised composite material of claim 16 wherein the soluble polymer containing one or more carboxylic acid groups comprises carboxylic acid groups on about 5 to 100% of monomers.

19. The mineralised composite material of claim 16 wherein the soluble polymer containing one or more carboxylic acid groups is selected from the group consisting of polyacrylic acid, polyaspartic acid, polylactic acid, polyglutamic acid, polymethacrylic acid, polyethylene glycol/polymethacrylic acid block co-polymers and mixtures thereof.

20. The mineralised composite material of claim 16 wherein the calcium carbonate comprises at least 40% aragonite.

* * * * *